United States Patent [19]

Olsen

[11] 4,434,157
[45] Feb. 28, 1984

[54] METHOD OF RECOVERING CELL ANTIGEN AND PREPARATION OF FELINE LEUKEMIA VACCINE THEREFROM

[75] Inventor: Richard G. Olsen, London, Ohio

[73] Assignee: The Ohio State University Research Foundation, Columbus, Ohio

[21] Appl. No.: 366,352

[22] Filed: Apr. 7, 1982

Related U.S. Application Data

[63] Continuation-in-part of Ser. No. 104,789, Dec. 18, 1979, Pat. No. 4,332,793.

[51] Int. Cl.$^3$ ............................................. A61K 39/12
[52] U.S. Cl. ..................................... 424/89; 435/183; 435/184; 436/543
[58] Field of Search ................. 424/89; 435/183, 184; 436/543

[56] References Cited

U.S. PATENT DOCUMENTS 4,086,134  4/1978  Jarrett et al. ......................... 195/1.2

FOREIGN PATENT DOCUMENTS 2951509  7/1980  Fed. Rep. of Germany .

OTHER PUBLICATIONS

Abraham Pinter; Preparation of Native Oncornavirus Envelope Subunits and Vaccines Therefrom; 1–12.
Richard G. Olsen et al.; In Vitro; 1976; 37–43.
Linda H. Wolff et al.; J. Natl. Cancer Inst.; Mar. 1977; 791–793.
Richard G. Olsen et al.; Cancer Research; Jul. 1977; 2082–2085.
Abraham Pinter et al.; Virology; 1977; 417–422.
Abraham Pinter et al.; Virology; 1978; 345–351.
Abraham Pinter et al.; Journal of Virology; Apr. 1979; 157–165.
Dres. J. W. Diaz et al.; Revista Cubana de Farmacia; 1978; 235–242.
T. Giraldi et al.; European Journal of Cancer, Oxford; 1977; 1321–1323.
D. J. Tweedie et al.; Biomedicine Express (See Biomedicine); 1978; 1–3.
R. Verloes et al.; Archives Internationales de Physiologie et de Biochimie Liege; 1976; 1119–1120.
A. Lupulescu; Experientia; 1980; 247–249.
A. Lage et al.; Neoplasma; 1978; 257–259.
A. L. Latner et al.; Experimental Cell Biology; 1979; 392–400.
Giuseppe Solarino; Tumori, Milan; 1967; 103–109.
A. L. Latner et al.; British Journal of Cancer, London; 1976; 535–538.
Mikrobiologichnyi Zhurnal Kiev; 1977; 751–end.
Gabriella Gamba et al.; Thrombosis Research; 1980; 41–53.
W. Troll et al.; Gesellschaft fuer Biologishe Chemie Colliquim; 1979; 165–170.
A. W. Thomson et al.; British Journal of Cancer, London; 1977; 454–460.
Vl. Kalaydjiev et al.; Zeitschrift fuer Immunitaetshforschung, Allergie und Klinische Immunologie Stuttgart; 1968; 98–103.
A. L. Latner et al.; British Journal of Cancer; 1974; 60–67.
A. M. Stewart; British Journal of Cancer, London; 1973; 460–464.
A. W. Thomson et al.; British Journal of Cancer; 1978; 106–113.
P. Whur et al.; British Journal of Cancer; 1973; 417–426.
Ingeburg E. Goetz et al.; Cancer Research; 1972; 2469–2474.
G. I. Ilyin; Patologicheskaia Fiziologiia i Eksperimental nava Terapiya; 1978; 16–19.
V. Kalaydjiev et al.; Proteases and Antiproteases in Cardioangiology, Int'l. Symposium, Vietri Sul Mare; 1969 (1970); 207–216.
Richard G. Olsen et al.; California Veterinarian; Mar. 1980; 11–13.
A. I. Volosivets et al.; Profilaktika Osobo Opasnykh Infektsii Saratov; 94–98.
E. V. Vlasova; Biulleten Eksperimental' Noi Biologii Meditsiny; 1969; 41–43.
Melinda J. Tarr et al.; Chemico-Biological Interactions; Dec. 1979; 181–199.
Arora Diss. Abstr.; Int. B. Sci. Eng. vol. 40/03, 1114 Ph. D. 1978, MSU Role of Protease Inhibitors in the Regulation of the Immune Response.

Gulyy et al., Molekulyarnaya Biolugiya (ID), 104–105, (1974), Enzyme Inhibitors and the Immune Response in Animals Uspto Translation.

Olsen et al., Feline Practice 9, (4):16–18, Jul.–Aug. 1979, Immunoprevention of Feline Leukemia.

Mathes, L. E. et al., Cancer Research 39(3):950–955, Mar. 1979, Immunosuppresive Properties of A Virion Polypeptide A 15,000 Dalton Protein from Feline Leukemia Virus.

Hebebrand et al., Cancer Research 39(2 pt 1): 443–447, Feb. 1979, Inhibition of Human Lymphocyte Mitogen and Antigen Response by a 15,000 Dalton Protein from Feline Leukemia Virus.

Lug T. Etal J. Immunol. Methods 26:291–303, (1979), Enzyme Immuno Assay for Focma and Detection of Focma in Cell Extract by Enzyme Immunoassay Inhibition Test.

C. A. 92: 278W, 127481 n, (1980) 90: 70408W, 52871n, 1153525, 16194K(1979), 89:71022g, 123142T(1978).

C. A. 88: 69685M, 58400p, 48921v(1978), 86:133639n, (1977) 85: 56679A, (1976), 82:332c(1975), 80: 2063y, (1974).

C. A. 79: 61449F, (1973), 78: 93115Q(1973), 77: 401W, 837356(1972), 70: 18482p(1969).

Jarrett "The Development of Vaccines Against Feline Leukemia", Origins of Human Cancer, pp. 1215–1272, (1977).

Wolff et al., Journal of Immunological Methods 26: 151–156, (1979), Recovery of Soluble Feline Oncornavirus–Associated Cell Membrane Antigen from Large Volumes of Tissue Culture Fluids.

*Primary Examiner*—Robert J. Warden
*Assistant Examiner*—Frederick W. Pepper
*Attorney, Agent, or Firm*—Millard & Cox

[57] ABSTRACT

Disclosed is a vaccine which prevents disease caused by Feline leukemia virus (FeLV) and which comprises a protease enzyme-inhibited, cell-free, ostensibly virus-free, in vitro produced feline leukemia neoantigens including FOCMA which evokes an immune response in cats by the appearance of antibodies thereto and a FeLV virion gp70 neoantigen which evokes an immune response in cats by the appearance of antibodies thereto. A novel method for making the vaccine is disclosed also.

13 Claims, 2 Drawing Figures

METHOD OF RECOVERING CELL ANTIGEN AND PREPARATION OF FELINE LEUKEMIA VACCINE THEREFROM

The invention described herein was made in the course of work under a grant or award from the Department of Health, Education and Welfare.

This application is a continuation-in-part of my copending application Ser. No. 06/104,789 filed Dec. 18, 1979, now U.S. Pat. No. 4,332,793, dated June 1, 1982.

BACKGROUND OF THE INVENTION

Viral-induced lymphoreticular neoplasms were first characterized in mice and rats, and later in chickens and turkeys. In 1964, viruses were also found to be associated with lymphoid malignancies of cats. The virus was named the Feline Leukemia Virus (FeLV). FeLV is classified as an oncornavirus (onco=oncogenic or cancer producing and RNA=ribonucleic acid). This virus is very unstable in the environment and seldom survives for more than several hours at room temperature. It is inactivated by most disinfectants. FeLV occurs in three antigenically similar types, A, B, and C, or combinations of these types.

Infection results by contact between infected and susceptible cats. Infected cats may appear totally asymptomatic or they man manifest feline leukemia disease. The incidence of infected cats in the general population is somewhat variable, but has been reported to be as low as a few of tenths of a percent to in excess of several percent depending upon locality. The incidence of infected cats in catteries well known FeLV-related diseases is much higher and has been reported to average 30% or more. The overall mortality to FeLV is proportional to the percentage of cats that become persistently viremic following exposure and infection. It is not surprising, therefore, that catteries and multiple-cat households have a greater loss than the general cat population because the carrier rate in these environments is much greater. In the general urban cat population, it has been estimated that the total death rate to FeLV could possibly be as high as 350 per 100,000. In catteries where FeLV is endemic, the death rate is potentially as high as 1 in 3 or more.

The pathogenesis of FeLV infection can be divided into three stages: primary disease, recovery or apparent recovery, and terminal illness. By and large, only those cats or kittens which eventually become persistently viremic will show significant clinical signs of illness in the primary stage of infection. Clinical symptons consist of varying degrees of fever, malaise, anorexia, weight loss, generalized lymphadenopathy, and hematological abnormalities. Death can occur in the primary stage of infection and when it does it is usually a direct consequence of severe bone marrow suppression and/or secondary infection. Cats that recover completely from the infection usually do not show any clinical or hematological abnormalities in the primary stage of the disease. In contrast, kittens or cats that develop clinical and hematological abnormalities during the primary stage of disease usually become persistent virus carriers. It is interesting to note that relatively few kittens or cats die as a result of this primary illness. In fact, most persistently infected cats will apparently recover from these primary symptons, giving the veterinarian and the owner a false sense that recovery is complete and that the virus has been eliminated. Carrier cats may remain asympomatic for weeks, months, years, or even an entire natural lifetime. Many of these cats, however, will eventually develop some FeLV-related disease.

Persistent virus carrier cats can be expected to develop a fatal FeLV-related illness at the rate of about 20% per year for every year they remain infected. The mortality can be greater if symptomatic treatment is not given, or if the animals are stressed. This means that about 50% of chronic FeLV carriers will be dead within four years or less. In addition to a fatal disease, persistent virus carriers frequently suffer from vague persistent or intermittent illnesses and secondary infections of a number of types. Those diseases related directly to the effect of the virus include neoplastic disease, bone marrow suppressive disorders, immunological disorders, reproductive problems, and various miscellaneous diseases. Those diseases indirectly related to FeLV infection include viral and bacterial secondary infections, protozoal diseases, and other maladies. In terms of total disease caused by FeLV, vague illness and secondary infections are the most frequent. This is followed in order of frequency by bone marrow supressive disorders, lymphoproliferative neoplasms, and myeloproliferative disease.

Prior proposals aimed at producing a vaccine for preventing FeLV include that of Jarrett ("The Development of Vaccines Against Feline Leukemia", *Origins of Human Cancer*, pp 1215–1222, 1977) and Jarrett et al (U.S. Pat. Nos. 3,966,907, 4,034,081, and 4,086,134) wherein the vaccine is based on virus which are killed (e.g. by irradiation, hydroxylamine, or paraformaldehyde) or inactivated (e.g. by mitomycin D) or based on whole live infected cells and inactivated infected cells. Pinter et al in *Viriology*, 83, 417–422 (1977) and 91, 345–351 (1978) and in *Journal of Viriology*, 30, 157–165 (1979) report the formation of non-denatured [gp90] a naturally occurring disulfide complex of gp70 and p15(E) virion antigens which may serve as the basis of a vaccine. None of these vaccines is truly effective in preventing disease caused by feline leukemia virus.

BROAD STATEMENT OF THE INVENTION

One aspect of the present invention is a method for recovering cell neoantigen associated with virus infected cells wherein said virus exhibits growth characteristics including noncytotoxicity and budding. Such method comprises culturing said infected cells in a serum-containing growth medium, transfering and maintaining said cultured cells in a serum-free medium under conditions and for a time adequate to accumulate in said serum-free medium cell neoantigens shed from said cells, separating said cells from said neoantigen-rich medium, concentrating at least said neoantigen in said neoantigen-rich medium, and inhibiting protease enzymes in said concentrate, preferably by adding an effective proportion of a protease inhibitor to said concentrated neoantigen. A further aspect of the present invention is the application of the foregoing method to the recovery of Feline leukemia associated neoantigen from cells infected with Feline leukemia virus.

A further aspect of the present invention is a vaccine for the prevention of disease caused by Feline leukemia virus (FeLV). Such vaccine comprises virus-free, protease enzyme inhibited, cell-free, in vitro produced FeLV-associated antigens including a FOCMA-type neoantigen which evokes an immune response in cats by the appearance of antibodies thereto, and a FeLV virion antigen of the gp70-type which evokes an immune response in cats by the appearance of antibodies thereto.

DETAILED DESCRIPTION OF THE INVENTION

Figure 1:
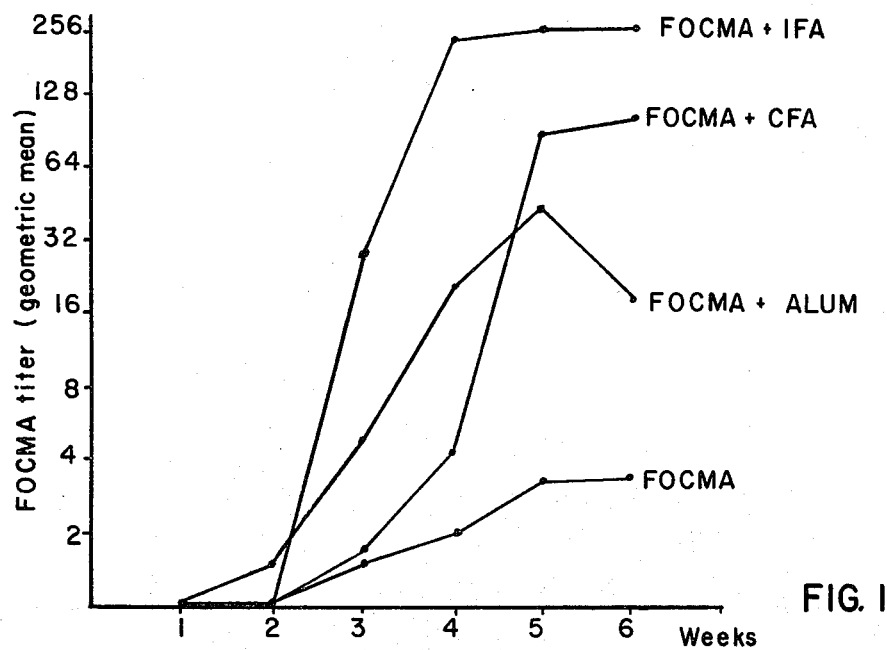
FIG. 1 depicts graphically responses of cats immunized with the vaccine emulsified in various adjuvants by plotting the FOCMA titers (geometric mean) as a function of time (weekly) following immunization, and will be described in connection with Example IV.

The vaccine of the present invention effectively protects cats against disease including FeLV virus and tumors associated therewith. Thus, not only is the cat protected against disease, but also the vaccinated cat is not a carrier of the virus. No other feline vaccine to date provides such protection.

In order that a full understanding of the invention can be gained readily, the following list of definitions for this application is given:

FOCMA: Feline Oncornavirus-associated Cell Membrane Antigen;

FeLV: Feline Leukemia Virus;

Budding: a process by which virus-infected cells release the virus from the cell surface;

gp70: FeLV glycoprotein with an approximate molecular weight of 70,000 daltons, the antibody to gp70 being capable of neutralizing the whole virus;

p27: FeLV core protein with an approximate molecular weight of 27,000 daltons;

p15 FeLV protein with an approximate molecular weight of 15,000 daltons and being an immunosuppressive protein associated with FeLV;

p12: FeLV protein with an approximate molecular weight of 12,000 daltons;

CCL64F3CL7: target mink cell that contains FeSV (feline sarcoma virus) and expresses FOCMA on its cell membrane but not virion proteins;

STCV: Soluble Tumor Cell Vaccine, the preferred feline leukemia vaccine of the present invention (see Example 1);

Neoantigen: an antigen not expressed by a normal or healthy cell, and for present purposes an antigen whose presence in the cell is associated with FeLV.

The present invention is based on several discoveries. One discovery is that milligram quantities of virus-associated antigens (neoantigens) can be recovered quickly and economically by a unique process described herein. Another discovery is a technique for implementing such neoantigen recovery process which makes the process, and thus the feline vaccine, amenable to remarkably economic, large-scale commercial production. A further discovery is that proteolytic enzymes in the recovered neoantigen undesirably act on such neoantigen in a relatively short time to effectively prevent any immune response to such neoantigen when such neoantigen is used as a vaccine. Thus, another discovery is that a protease inhibitor added to such neoantigen effectively preserves the activity of the neoantigen. Yet another discovery is that the neoantigen recovery process apparently has broad applicability to the recovery of cell neoantigen produced by cells infected with a virus which exhibits growth characteristics of budding and noncytotoxicity. These and other discoveries and their implementation which forms the present invention will be described in detail below.

Referring to the method for recovering milligram quantities of virus-associated antigens (neoantigens), a convenient cell line for use in such neoantigen recovery process is derived from infected cells taken from the infected animal. Thus, lymphoid or lymphoblastoid feline cells are convenient for use in recovering neoantigens associated with feline leukemia by the present invention. Alternatively, use of glass-adherence cells especially as monolayers grown on beads in suspension or use of in vitro infected normal cells may find applicability in the process. A prime requirement of the infected cells used is that a high concentration of such cells can be grown in effective suspension in a growth medium. Thus, effectively suspended glass-adherence cells on beads fulfill this requirement as do infected normal cells. Those normal cells which may find suitability for infection for use in the process may be described as permissive cells which bud the virus where such virus is noncytotoxic to such cells. It should be understood that noncytotoxic viruses include not only those viruses conventionally described as noncytotoxic, but also genetic virus aberrants which are normally cytotoxic but which are noncytotoxic on the particular cell line of choice to be infected by such virus.

That the cell-synthesized neoantigen can be recovered by the present invention is through a fortuitous circumstance or principle of nature that cell surface neoantigens are continually shed from appropriate cells as such cells proceed through their normal growth cycle (Olsen et al, In Vitro 12:13-43, 1976). However, as revealed herein, the recognition of such principle is insufficient without an appropriate process for the practical implementation of a process which operates based upon such principle. As a first step in the process, the infected cells of choice are placed in a serum-containing growth medium for their culturing. Such serum-containing growth medium comprises a conventional serum-free growth medium having added thereto an appropriate quantity of animal serum, such as fetal bovine serum. Appropriate serum-free media include McCoy's 5a medium, RPMI 164 medium, and like conventional media. To such serum-free medium are added appropriate quantities of serum and antibiotics in conventional fashion. The cells are cultured in such medium, with additional serum optionally added from time to time, preferably until such cells have reached saturation density in the volume of medium used. Conventional growth conditions are maintained as such conditions are well known in the art.

The next step of the process is based on one of the fundamental discoveries upon which the present invention is based. Such step comprises transferring the cultured cells to a serum-free growth medium of composition substantially the same as that used in the culturing step of the process except that no serum is used or added at this step of the process. The cells placed in the serum-free medium apparently cease their normal growth cycle and apparently virtually all viral production additionally is arrested. The cells, it is hypothesized, are subjected to severe stress in the serum-free medium so that an abundance of proteins and additional matter including neoantigen is shed from such cells in substantial quantities. Milligram quantities of neoantigen can be released from such cells in but a few days while such cells are maintained in the serum-free medium. Avoidance of serum at this point in the process removes potential allergenic factors which serum often evidences if found in vaccines.

The neoantigen-rich serum-free medium then is subjected to a separation step for separating the infected cells from the supernatant or neoantigen-rich medium. The conventional or preferred method for implementing this separation step of the process is by subjecting the neoantigen-rich serum-free medium to centrifugation at, for example, about 200–500 x g. for about 15 minutes. It will be appreciated that the precise conditions of centrifugation may vary depending upon the volume of medium subjected to the process, the concentration of cells in such medium, and similar factors well known in the art. It has been determined that the neoantigen remains in the cell-free supernatant by virtue of the centrifugation process. It is believed that the neoantigen is soluble in the aqueous supernatant because it appears to conform to the definition of solubility (i.e. it remains in the supernatant when subjected to centrifugation at 100,000 x g. for one hour). However, whether the neoantigen is soluble (under the foregoing definition) or remains as a dispersion or suspension in the supernatant is of no critical consequence for the present invention as the neoantigen remains in the supernatant during the centrifugation process as is required. It should be noted that the separated cells used in the vaccine process may be used for further vaccine production by their reconstitution with complete growth medium. Additionally, the initial serum-containing growth medium optionally may be combined with fresh growth medium for recycling to the initial step of the process to further economize the production costs of the process and resulting vaccine.

The resulting centrifuged neoantigen-rich serum-free medium or supernatant can be processed by a variety of techniques, many of which are convenetional in the art. Thus, the neoantigen-rich medium may be subjected directly to lyophilization, dialysis followed by lyophilization, ultrafiltration optionally followed by lyophilization, or like techniques. Considering the probable large volume of supernatant which must be processed, especially for commercial implementation of the invention the distinctly preferred technique for processing the neoantigen comprises subjecting the cell-free, neoantigen-rich, serum-free medium to concentration by continuous-flow molecular filtration such as described by Wolff et al, *Journal of Immunological Methods*, 26, 155–156 (1979). A maximum exclusion size of the filter of about 10,000 daltons has been determined to be suitable in implementing this step of the process. That material greater than the indicated exclusion size (i.e. the retenate) contains the desired neoantigen and is retained. The molecular filtration concentration step can be practiced to typically concentrate the supernatant from about 20× to 400× or thereabouts, although variation from this range certainly is comprehended within the spirit of the present invention. The distinctly preferred molecular filtration concentration step of the present invention provides several distinct advantages which may not be readily apparent. One of the advantages is based on the fact that the diseased cells initially are grown under physiological conditions and it is preferred to maintain such conditions during the processing of the neoantigen. Molecular filtration, as practiced in the present invention, provides the ability to concentrate all material in size larger than the exclusion size of the filter used while maintaining substantially the same ion concentration of the supernatant passed therethrough. This supernatant contains various salts, amino acids, and the like which provide or contribute to the physiological conditions or state established in the initial culturing step of the process and such ionic material can be kept at approximately the same concentration by the molecular filtration step. Water is the prime ingredient of the supernatant fed to the molecular filtration step of the process which is removed.

Further processing of the molecularly-filtered neoantigen concentrate can take several routes. The neoantigen concentrate can be conventionally dialyzed for removal of salts and then subjected to lyophilization, can be directly lyophilized, or can be subjected to additional conventional concentration techniques well known in the art. Regardless of the concentration route chosen, the neoantigen concentrate desirably is frozen and lyophilized with a shell-freezing technique being preferred though not necessary. The neoantigen powder can be stored in such form or can be resuspended and stored at very low temperatures (e.g. −90° C.) as is necessary, desirable, or convenient.

Regardless of the particular concentration technique employed, a prime and critical step of the invention is based on the discovery that the recovered neoantigen concentrate must have enzymatic activity towards the neoantigen abrogated, because protease enzymes suppress any immune response in cats to the antigen concentrate. The distinctly preferred technique presently employed to suppress such protease enzymes is by the addition of a protease inhibitor to the neoantigen concentrate. It must be recognized, however, that other techniques may prove effective in abrogating the protease enzymes activity on the neoantigen such as, for example, heat, physiological conditions (e.g. pH or ionic strength), etc. Such protease inhibitor can be added to the cell-free supernatant prior to concentration, can be added to the concentrate such as is produced by the preferred molecular filtration step of the process, or can be added to the reconstituted neoantigen preparation following lyophilization. The precise point during the preparation of the neoantigen at which the protease inhibitor is added appears not to be critical, though its addition at some point of the process is critical. Conventional broadbased protease inhibitors include aprotinin, antipapain, leupeptin, ovomucoid, soybean trypsin inhibitor, tolyl-L-lysine chloromethylketone, and the like. For FeLV infected cells fed to the process, a vaccine results upon the addition of the protease inhibitor to the neoantigen preparation.

The techniques which may be used to inhibit the protease enzymes in the instant vaccine are similar to those previously known in the art, for example the denaturation techniques described in White A., Handler, P. and Smith, E. L., Principles of Biochemistry, 3rd edn., McGraw Hill, New York (1964) pp. 136–137.

The foregoing procedure additionally can be used to produce neoantigen concentrates and vaccines for other virus systems. Viruses with growth characteristics similar to FeLV are the best candidates for use in the process. Such viruses are those which do not cause cell death (cytotoxicity) during its growth cycle and are those that are released from the cells by a budding process, those growth characteristics possessed by FeLV. The following is an illustrative list of viruses which have the indicated growth characteristics and are applicable to the neoantigen preparation process of the present invention:

| Retroviruses | Coronavirus Group |
|---|---|
| Avian leukosis virus | Transmissible gastroenteritis virus |
| Bovine leukemia virus | |
| Equine infectious anemia | Feline infectious peritonitis |
| Aleutian mink disease virus | |
| Herpesviruses | Rhabdovirus Group |
| Pseudorabies (Aujeszky's disease) virus | Rabies virus |
| Infectious bovine rhinotracheitis virus | |
| Varicella virus | |
| Equine rhinopneumonitis (equine abortion) virus | |
| Malignant catarrh virus of cattle | |
| Bovine ulcerative mammillitis (Allerton) virus | |
| Feline rhinotracheitis virus | |
| Canine herpesvirus | |
| Epstein-Barr virus | |
| Marek's disease virus | |
| Infectious laryngotracheitis (avian) | |
| Avian herpesviruses | |
| Sheep pulmonary adenomatosis (Jaagsieket) virus | |
| Cytomegalovirus | |

Referring now to the vaccine for the prevention of disease caused by feline leukemia virus, such vaccine is cell-free, in vitro produced feline leukemia-associated antigens with a protease inhibitor added thereto. The vaccine contains no infectious virus particles and is believed to be virtually virus-free. The FeLV-associated neoantigens include a FOCMA-type neoantigen which evokes an immune response in cats by the appearance of antibodies thereto and a FeLV virion antigen of the gp70-type which evokes an immune response in cats by the appearance of antibodies thereto. A complete characterization and work-up of the neoantigens in the vaccine will be provided in the examples which follow. Suffice it to say here that the indicated neoantigens have been confirmed to be present in the vaccine as well as antibodies thereto confirmed to be present in cats immunized with the vaccine. Additionally, it must be noted that the p15 antigen, the immunosuppressive protein associated with FeLV, additionally has been determined to be present in the vaccine with corresponding p15 antibodies determined to be present in a cat vaccinated with the vaccine. It is believe that the presence of the p15 antigen is not necessary for the vaccine to be effective in the prevention of FeLV disease and certainly no apparent immunosuppressivity is exerted by any antigen contained in the vaccine. As shown in Example III below, the instant vaccine may also contain a p12 antigen. Example III also shows that the aforementioned p15 and p12 antigens may be present in a precursor form having a molecular weight differing from that of the natural antigen. Accordingly, the terms "p15 neoantigen" and "p12 neoantigen" are used hereinafter to refer to such antigens in both the natural and precursor forms. Also, as will be indicated in the characterization of the vaccine in the Examples, the p27 core protein of the virus additionally is found to be present in the vaccine. Use of the expression "FOCMA-type neoantigen" is deemed appropriate because the art, while confirming the presence of a FOCMA antigen in the diseased cell, at times appears to redefine or alter the definition of FOCMA. For present purposes, a precise label of the FOCMA neoantigen is deemed unnecessary in that its presence is confirmed as measured by the immune response in cats by the appearance of antibodies thereto. Also, the term "FeLV virion neoantigen" is deemed appropriate since the gp70 neoantigen found in the vaccine, as well as other virion proteins contained therein, may be in a precurser or nonmature form. Whether or not this precurser gp70 protein form or the gp70 protein itself is in the vaccine is not limitative of the vaccine, because the gp70-type protein in the vaccine is confirmed and determined by the immune response evoked in cats by the appearance of antibodies thereto, as will be shown in the examples which follow.

In any event, efficacy testing has demonstrated that the vaccine, desirably emulsified in appropriate adjuvants or non-specific immunostimulators, elicits antibody responses to FOCMA and FeLV virion neoantigen and provides to vaccinated cats at least about 80% protection from an FeLV challange that produced a 100% incidence of disease in nonvaccinated control cats. Although the use of Complete and Incomplete Freund's adjuvants are described in the Examples below, those skilled in the art will appreciate that these adjuvants are not clinically acceptable for normal use. However, those skilled in the art will also be aware that numerous other clinically-acceptable adjuvants are available for use in the instant vaccines.

Vaccination age of the cats has been determined not to be related to the effectiveness of the vaccine. That is, kittens and adult cats both can be vaccinated with the vaccine and full protection from infection provided thereby. The preferred minimum age of the kitten for inoculation, as with most other vaccines, is at about 8 weeks when the kitten has been weaned and maternal antibody disappeared from the kitten, though kittens vaccinated as young as 4 weeks have proved to be protected from feline leukemia disease. Further, the particular type of non-specific immunostimulator or adjuvant utilized for the vaccine can be conventional and such adjuvants include, for example, incomplete Freund's adjuvant, complete Freund's adjuvant, alum, or the like.

The following Examples will show how the present invention can be practiced, but should not be construed as limiting. Also, all units herein are in the metric system and all references cited are incorporated expressly herein by reference.

EXAMPLE I

This example demonstrates the recovery of feline leukemia-associated neoantigen from cells infected with Feline leukemia virus.

The cell line of choice was the FL-74 cell line originally derived from a Kawakami-Theilen Feline Leukemia Virus (KT-FeLV) - induced cat lymphoma. The FL-74 cells are cultured in roller bottles by seeding the cells at a concentration of $1.6 \times 10^6 - 1.8 \times 10^6$ cells/ml in each bottle which contains 200 ml of McCoy's 5A suspension medium with 10–25% fetal bovine serum, gentamicin sulfate (50 $\mu$g/ml), and Amphotericin B (30 $\mu$g/ml). After four days of culturing, the cells are fed with 200 ml of fresh medium containing 10% fetal calf serum.

The cells, once grown to a saturation density of $4-5 \times 10^6$ cells/ml, are washed three times in serum-free McCoy's 5A medium with antibiotics as above and resuspended in the serum-free medium (without any serum) to the original concentration. Cells are maintained for an additional four days at an optimum temperature of 37° C. To harvest the released neoantigen, the culture fluid is clarified by centrifugation at 16,000×g for 15 minutes.

The preferred procedure used for processing antigen from cell culture fluid is carried out by continuous-flow molecular filtration. The molecular filtation system was equipped with a five square foot (0.45 square meter) membrane cassette having an exclusion size of approximately $10^4$ daltons. Flow of cell culture fluid through the filtration unit was facilitated by use of a high volume peristaltic pump. The antigen-rich supernatant was concentrated by recycling it through the filtration system until the volume of the supernatant was reduced to approximately 1/20 of the original volume. Between runs, the membrane was washed in the assembled molecular filtration cell with four liters of distilled water followed by pumping one liter of 1 N NaOH into the system and allowing the caustic to stand for two hours. The caustic then was removed and the system rinsed again with several liters of water. For decontamination, the filtration system was flushed with 2% formalin.

The concentrated antigen preparation was reduced in volume further by lyophilization. The 20X concentrate was first dialyzed three consecutive days with three four-liter volumes of distilled demineralized water in order to remove the salts therefrom. Alternatively, salts could have been removed by column filtration using an appropriate desalting matrix or by a similar conventional processing. The desalted-concentrate then was shell-frozen and lyophilized. The resulting antigen preparation was resuspended in saline to 1/200 of the original volume. The saline contained aprotinin protease inhibitor (about 60 Trypsin Inhibitor Units) in a proportion so that the final antigen preparation contained a concentration of about 10% of such protease inhibitor. The antigen preparation then was stored at $-90°$ C. Such antigen preparation is the vaccine of the present invention and often will be referred to as STCV in the other examples which follow.

EXAMPLE II

This example compares three different techniques which may be used to concentrate the antigen-rich serum-free medium.

In the first concentration technique A, the clarified neoantigen was centrifuged at 100,000×g for 1 hour and then concentrated by dialysis in cellulose membrane tubing against polyethylene glycol (Aquacide III, Calbiochem, La Jolla, Calif.). In the second concentration technique B, the clarified neoantigen was centrifuged at 100,000×g for 1 hour, subjected to salt removal by dialysis in cellulose membrane tubing using 2 changes of 5 volumes of buffer (0.01 M Tris, pH 7.6) each, and finally lyophilized and reconstituted in the manner described in Example I. In the third concentration technique C, the continuous flow molecular filtration technique of Example I was followed by centrifugation at 100,000×g for 1 hour, salt removal as in technique B, and lyophilization and reconstitution as in technique B.

The indirect membrane immunofluoroescence (IMI) (Essex et al, *Ing. J. Cancer*, 8:384, 1971; Olsen et al, *In Vitro*, 12:37, 1976) and microcytotoxicity (Mathes et al, *J. Natl. Cancer Inst.*, 56:1197, 1976) assays were used to quantitate antibody specific for the cell surface of feline leukemia virus-transformed cells. Antigen was quantified using a cytotoxicity inhibition assay reported by Wolff et al (*J. Natl. Cancer Inst.*, 58:791, 1977). The reference cat antiserum used was shown to be specific for FOCMA since adsorption of the serum with intact and ether disrupted KT-FeLV ($10^{11}$ particles of each per ml of serum) did not decrease antibody titers in the membrane immunofluorescence or microtoxicity tests. Protein was quantified using the Bio-Rad Protein assay kit (Bio-Rad Laboratories, Richmond, Calif.).

The results obtained for the concentration tests are displayed below.

TABLE I

Comparison of FOCMA Yields When Using Three Different Concentration Techniques

| Technique | Concentration Factor | Protein (mg/ml) | Specific Activity (U/mg Protein) | Antigen (U)[1] per ml. | Antigen (U) per ml at comparable concentration (400 X) |
|---|---|---|---|---|---|
| A | 200 X | 14.6 | 42 | 609 | 1218 |
| B | 200 X | 13.2 | 26 | 343 | 686 |
| C | 400 X | 14.5 | 42 | 625 | 625 |

[1]One antigen (U) is defined as the mg of protein in 25 mg that inhibits by 50% the cytotoxicity activity of FOCMA-positive antisera.

The above-tabulated results demonstrate that several different techniques exist for concentrating the antigen-rich, serum-free medium following cell removal. The antigen yield obtained by lyophilization alone (Technique A) was twice that obtained by dialysis (Technique B) or molecular filtration (Technique C). However, for the handling the large volumes of fluid necessary for commercial implementation of the process, molecular filtration (Technique C) clearly was the easiest to carry out. Moreover, it required only 4 hours to concentrate 6 liters of fluid 15 times by such filtration technique. It is to be noted that no protease inhibitor was added to the concentrates prepared in this example as none is required in order to simply quantify neoantigen yield by the process of the present invention.

EXAMPLE III

This example provides characterization of the FeLV virion antigens in the vaccine.

Specific antisera to FeLV virion proteins were used to identify particular virion proteins in the vaccine preparation. In this procedure, antisera to FeLV p15, p27 and gp70 were reacted with $^{35}S$ methionine labeled vaccine. Immune complexes were collected by adherence to *Staphlococcus aureus* and the $^{35}S$ labeled protein disociated and electrophoresed on SDS polyacrylamide slab gels. After electrophoresis, the gels were subjected to radiofluorography. The results indicated that p15 was not present in the natural form. Instead, a faint band of 20,000–25,000 daltons M.W. was observed. gp70 and p27, however, were detected as natural proteins of 70,000 and 27,000 M.W., respectively. Additional tests were carried out using anti p12. Because p12 apparently labels poorly with $^{35}S$ methionine, no band was detected when $^{35}S$ labeled FeLV was reacted with anti p12. However, anti p12 did recover a protein of 80,000–90,000 daltons and was reacted with the $^{35}S$-vaccine preparation. Thus, virion proteins p15 and p12 appear to be in precursor protein form in the vaccine preparation. p15 is in a 20,000–25,000 M.W. form while p12 is recovered in a 80,000–90,000 M.W. form. p27 and gp70 apparently are present in natural forms.

EXAMPLE IV

This example provides the efficacy testing results derived by use of a vaccine (STCV) as prepared according to the process described in Example I.

Two groups of cats were used for the efficacy testing of the vaccine. The first batch of cats were experimental cats obtained from the SPF (specific pathogen free) facilities at the Ohio State University. The cats varied in age from 4 weeks to 5 years at the beginning of the vaccination. All cats received a vaccination regimen consisting of five weekly immunizations with the vaccine mixed with either complete Freund's adjuvant (CFA), incomplete Freund's adjuvant (IFA), Alumhydroxin gel, or no adjuvant. The control batch received one of these adjuvants plus 1640 RPMI medium. All cats were challenged six weeks after first immunization. The challenge consisted of an oral-nasal administration of tumor homogenate in conjunction with an intra-muscular injection of Depo-medrol (10 mg/kg body weight). The challenge was given on two consecutive days. All cats were monitored weekly for FeLV viremia status and antibody titers towards FL-74 and CCL64F3CL7 mink cells. Antibody titers were determined by indirect membrane immunofluorescence (IMI) by the procedure described by Essex et al, 1971 supra, and by Olsen et al, 1976 supra. All vaccinated cats were housed with control littermates.

The second batch of cats consisted of 24 normal household cats which were vaccinated with the vaccine containing complete Freund's adjuvant. A total of five immunizations were given over a six week period. All of these household cats either were viremic or had exposure to viremic cats at the beginning of vaccination.

Table 1 is a complete analysis of the immunoprophylactic value of the STCV emulsified in CFA. Where possible, kitten litters were equally divided between vaccinated and controls.

TABLE 1[1]

Immunologic Response to FOCMA and Protection from FeLV Disease in Cats Immunized with STCV Emulsified in CFA

| Litter and Cat No. | Control[2] FeLV Viremia BC | AC | IMI Antibody Titer on FL-74 BC | AC | 64F3CL7 BC | AC | Vaccinated[3] FeLV Viremia BC | AC | IMI Antibody Titer on: FL-74 BC | AC | 64F3CL7 BC | AC |
|---|---|---|---|---|---|---|---|---|---|---|---|---|
| 603B-1 |  |  |  |  |  |  | — | — | 64 | 256 | 8 | 16 |
| 603B-2 |  |  |  |  |  |  | — | — | 32 | 32 | 8 | 32 |
| 603B-3 | — | + | — | 4 | — | — |  |  |  |  |  |  |
| 603B-4 | — | + | — | 4 | — | — |  |  |  |  |  |  |
| 1077B-1 |  |  |  |  |  |  | — | — | 256 | 256 | 8 | 32 |
| 1077B-2 |  |  |  |  |  |  | — | — | 128 | 128 | 32 | 32 |
| 1077B-3 | — | + | — | 8 | — | — |  |  |  |  |  |  |
| 1077B-4 | — | + | — | 4 | — | — |  |  |  |  |  |  |
| 102-1 |  |  |  |  |  |  | — | — | 32 | 128 | 32 | 32 |
| 102-2 |  |  |  |  |  |  | — | — | 256 | 256 | 32 | 32 |
| 607B |  |  |  |  |  |  | — | — | 256 | 256 | 8 | 16 |
| 956B |  |  |  |  |  |  | — | + | 256 | 32 | 32 | 16 |
| 603B | — | + | — | 4 | — | — |  |  |  |  |  |  |
| 115B | — | + | — | 16 | — | — |  |  |  |  |  |  |
| 821B | — | + | — | 4 | — | — |  |  |  |  |  |  |
| 742B |  |  |  |  |  |  | — | + | 128 | 128 | 32 | 4 |
| 700B |  |  |  |  |  |  | — | — | 32 | 256 | 16 | 32 |
| 811B |  |  |  |  |  |  | — | — | 256 | 256 | 4 | 4 |
| 719B |  |  |  |  |  |  | — | — | 128 | 256 | NT | NT |
| 102 |  |  |  |  |  |  | — | — | 32 | 128 | NT | NT |
| 1136B |  |  |  |  |  |  | — | — | 256 | 128 | NT | NT |
| Geometric Mean |  |  | 0 | 6.3 | 0 | 0 |  |  | 94.5 | 152.2 | 19.0 | 22.6 |
| % Viremia | 0 | 100 |  |  |  |  | 0 | 18.75 |  |  |  |  |

[1]BC: Before Challenge; AC: After Challenge; NT: Not Tested
[2]All cats administered CFA in cell culture medium
[3]All cats vaccinated with STCV emulsified in CFA.

The above-tabulated results show that all cats vaccinated with the STCV plus CFA developed high antibody titers to FL-74 cells with the mean titer being 94.5 before challenge. All of the vaccinated cats also showed an antibody response to FOCMA on CCL64F3CL7 mink cells. Antibody titers remained the same or increased in all of the vaccinated cats after challenge except in the cats that became persistently viremic. The three cats that became viremic had the same or lower antibody titers, but remained healthy. Control cats developed no antibody titers to either FL-74 or CCL64F3CL7 cells before challenge. All cats that became persistently viremic converted within three weeks after challenge. Only the vaccinated adults showed any detectable transient viremia. The antibody titers of the vaccinated kittens decreased after challenge and did not begin to rise again until 6 to 22 weeks after challenge. Note that prior testing had revealed that use of the neoantigen concentrate without protease inhibitor to vaccinate 4 week old kittens showed that the highest geometric mean FOCMA antibody titer achieved was only 1:20 and protection from FeLV disease was not provided to the kittens.

Table 2 summarizes the results obtained from the immunization of cats with the vaccine alone (i.e. with no adjuvant).

TABLE 2[1]

Immunologic Response to FOCMA and Protection from FeLV Disease in Cats Immunized with STCV with No Adjuvant

| Litter and Cat No. | Control[2] | | | | | | Vaccinated[3] | | | | | |
|---|---|---|---|---|---|---|---|---|---|---|---|---|
| | FeLV Viremia | | IMI Antibody Titer on: | | | | FeLV Viremia | | IMI Antibody Titer On: | | | |
| | | | FL-74 | | 64F3CL7 | | | | FL-74 | | 64F3CL7 | |
| | BC | AC | BC | AC | BC | AC | BC | AC | BC | AC | BC | AC |
| 123B-1 | | | | | | | — | — | 32 | 8 | 4 | — |
| 123B-2 | | | | | | | — | — | 64 | 8 | 2 | — |
| 123B-3 | — | + | — | — | — | — | | | | | | |
| 943-1 | | | | | | | — | + | 16 | 4 | 16 | — |
| 943-2 | | | | | | | — | + | 4 | — | — | — |
| 943-3 | — | + | — | — | — | — | | | | | | |
| 719B-1 | | | | | | | — | + | — | — | — | — |
| 719B-2 | | | | | | | — | — | 8 | 8 | NT | NT |
| 719B-3 | — | + | — | — | — | — | | | | | | |
| 811B-1 | | | | | | | — | — | 16 | 16 | — | — |
| 847B-1 | — | + | — | 4 | — | — | | | | | | |
| 847B-3 | | | | | | | — | — | 64 | 64 | 16 | 16 |
| 514 | | | | | | | — | — | 32 | 128 | 32 | 32 |
| 92R | | | | | | | — | + | 8 | 4 | 16 | 16 |
| 123B | | | | | | | — | + | 8 | 256 | 4 | 2 |
| 943 | | | | | | | — | — | — | 128 | 4 | 4 |
| 850B | | | | | | | — | — | 4 | 16 | NT | NT |
| Mean Antibody Titer | | | 0 | 1.2 | 0 | 0 | | | 9.9 | 13.6 | 5.9 | 4.4 |
| % Viremia | 0 | 100 | | | | | 0 | 38.5 | | | | |

[1]BC: Before Challenge; AC: After Challenge; NT: Not Tested
[2]All cats administered only cell culture medium.
[3]All cats vaccinated with STCV only.

The above-tabulated results demonstrate that the antibody titers were much lower for the vaccine alone than those antibody titers developed by the cats vaccinated with the vaccine plus CFA. One kitten showed no detectable response, though. Four of the five cats that became persistently viremic showed minimal response to the vaccine before challenge (1:8). All of the control cats became viremic within three weeks after challenge. The five vaccinated cats that became viremic had a mean conversion time of 4.6 weeks with a range of between 2 and 8 weeks.

Tables 3 and 4 summarize the results obtained from inoculation of the vaccine plus alumhydroxin gel (Table 3) or IFA (Table 4).

TABLE 3

FOCMA Antibody Response in Cats Immunized with STCF Emulsified in Alumhydroxin Gel

| Cat Number | Mean Highest IMI Antibody Titer to FOCMA On: | |
|---|---|---|
| | FL-74 | Mink 64F3CL7 |
| 781B | 16 | 4 |
| 781B-1 | 16 | 4 |
| 781B-2 | 32 | 8 |
| 781B-3 | 8 | 4 |
| 966B | 256 | 16 |
| 966B-1 | 32 | 16 |
| 966B-2 | 32 | 8 |
| 1092B | 256 | 8 |
| 913B | 256 | 8 |
| 1230B | 128 | 8 |
| 1274B | 256 | 4 |
| Mean Antibody Titer | 60.14 | 7.1 |

TABLE 4

FOCMA Antibody Response in Cats Immunized with STCV Emulsified in IFA

| Cat Number | Mean Highest IMI Antibody to FOCMA On: | |
|---|---|---|
| | FL-74 Cells | Mink 64F3CL7 |
| 987B-1 | | 16 |
| 987B-2 | 256 | 8 |
| 987B-3 | 256 | 8 |
| 1114B | 256 | 8 |
| 1114B-1 | 256 | 16 |
| 1114B-2 | 256 | 4 |
| 1158B | 256 | 8 |
| 1158B-1 | 256 | 4 |
| 1158B-2 | 256 | 8 |
| Mean Antibody Titer | 256 | 8 |

The above-tabulated results show that all cats immunized with these vaccines developed high antibody titers to FL-74 and CCL64F3CL7 target cells.

Table 5 summarizes the results from Tables 1-4 in which a total of 49 experimental cats were immunized with the vaccine emulsified in various adjuvants.

TABLE 5

Summary of a Comparative Study of Responses of Cats Immunized with STCV Emulsified in Various Adjuvants

| Number of Cats | Vaccination Regimen | Number Viremic | Geometric Mean Antibody Titer On: | | | |
|---|---|---|---|---|---|---|
| | | | FL-74 Cells | | 64F3CL7 | |
| | | | BC | AC | BC | AC |
| 9 | Media + CFA | 13 | 2 | 4 | 2 | 2 |
| 4 | Media | 13 | 2 | 4 | 2 | 2 |
| 13 | STCV | 5 | 10 | 14 | 6 | 4 |
| 16 | STCV + CFA | 3 | 95 | 152 | 19 | 23 |
| 11 | STCV + Alumhydroxy | N.C.[1] | 60.1 | N.A.[2] | 7.1 | N.A. |

TABLE 5-continued

Summary of a Comparative Study of Responses of Cats Immunized with STCV Emulsified in Various Adjuvants

| Number of Cats | Vaccination Regimen | Number Viremic | Geometric Mean Antibody Titer On: | | | |
|---|---|---|---|---|---|---|
| | | | FL-74 Cells | | 64F3CL7 | |
| | | | BC | AC | BC | AC |
| 9 | STCV + gel IFA | N.C. | 256 | N.A. | 8 | N.A. |

(1)N.C. = not challenged with FeLV
(2)N.A. = not applicable

The above-tabulated results shows that all 13 cats that received media emulsified in CFA did not produce FOCMA antibody; moreover, after challenge, all 13 cats became persistently viremic. The vaccine either alone or emulsified in adjuvants elicited potent antibody responses in kittens and adults to FOCMA. Both the vaccine alone and the vaccine emulsified in CFA produced significant protection in kittens and adults to FeLV challenge (62% and 81% respectfully). The results obtained as reported in Table 5 is depicted in FIG. 1 which is a plot of the FOCMA titer (geometric mean) obtained weekly up to six weeks following the vaccination regimen.

Table 6 summarizes the results from vaccinations of the household cats.

TABLE 6

Vaccination of Household Cats with STCV

| Cats Vaccinated | Number Tested | Mean IMI Titer to FOCMA on FL-74 | |
|---|---|---|---|
| | | Before Vaccination | After Vaccination |
| Cats with confirmed FeLV infection (asymptomatic) | 16 | 1.68 | 11.81 |
| Cats that are viremia negative but exposed to other FeLV-viremic household cats | 8 | 1.30 | 41.4 |

In the tests reported in Table 6, the viremic group of cats consisted of 16 adults. Six weeks after the first vaccination, all of these cats showed significant increases in antibody titers to FL-74 cells. Only one cat in this group died. All of the remaining cats showed a drop in antibody titer to FL-74 cells one month after the vaccination regimen was completed and are asymptomatic for FeLV disease. The viremia negative group consisted of 8 adult cats all of which developed antibody titers to FL-74 cells ranging from 1:4 to 1:256 with a mean of 41.4. These cats have had prolonged exposure to at least one viremic cat prior to vaccination. To date, none of these cats have shown signs of FeLV disease.

EXAMPLE V

This example provides characterization of the FeLV virion antibody developed by cats vaccinated with the vaccine emulsified in CFA.

Sulfur 35 methionine-labeled FeLV was derived from FL-74 cells. One day old cultures of FL-74 cells grown in suspension in flasks containing McCoy's 5 A medium and 10% fetal calf serum were collected by centrifugation and washed once with and resuspended in 40 ml methionine deficient (1:50 normal concentration) 5 A medium containing 10% dialyzed FCS. After 24 hours, 0.04 ml of 0.1 M solution of methionine was added to the culture vessel. After 48 hours, the culture fluids were collected by centrifugation and concentrated 4X by dialysis against polyethene glycol. The concentrate (10 ml) was applied to the top of a 0 to 50% sucrose gradient (29 ml) and TNE buffer (0.01 M Tris, 0.1 M NaCl, 0.001 M EDTA ph 7.4) and centrifuged for one hour at 100,000 X g. The gradient then was fractionated into 1 ml volume and the virus collected in the 1.16 g/cm$^3$ region. Sucrose was removed from the resulting virus by dialyzing overnight against 10 volume TNE.

Serum samples to be tested for antibody to gp70, p27, p15, and p12 were diluted 1 to 4 in NP-40 buffer [0.01% NP-40 in NET Buffer (0.15 M NaCl, 0.005 M EDTA, 0.05 M Tris)] (100 μl total) and added to 50 μl of $^{35}$S-labeled FeLV. The mixture was allowed to incubate overnight at 4° C. with constant agitation. Immune complexes were recovered using Cowin I strain *Staphylococcus aureus* as described by Kessler [J. Imm., 115:1617 (1975)]. Fifty μl of killed *Staphylococcus aureus* was added to each tube and agitated for 24 hours at 4° C. The *Staphylococcus aureus* then was washed three times by centrifugation with NP-40 buffer. Immune complexes were suspended by the final centrifugation pellets in tris-T-acetate buffer containing SDS and DTT, and heated to 100° C. for 5 minutes. The SDS PAGE system used 12 cm slab gel consisting of 7.5% acrylamide with 5% bisacrylamide. One hundred μl samples were applied to the top of the gels and electrophoresed for 4.5 hours at a constant 100 volts. Gel slabs were dried in a gel dryer.

Figure 2:
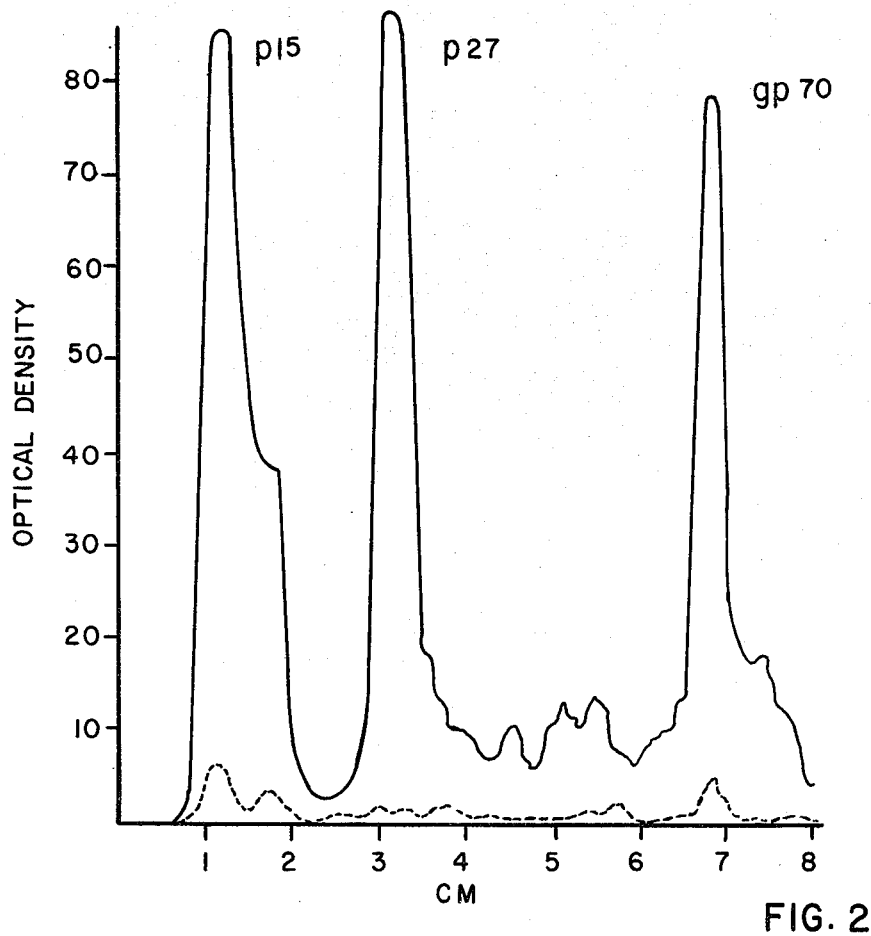
FIG. 2 depicts fluorography results for identifying the FeLV virion antibodies developed by cats vaccinated with the vaccine emulsified in Complete Freund's adjuvant and will be described in connection with Example V.

The fluorography technique utilized was that described by Bonner and Laskey [*Eur. J. Biochem,* 46:83–88 (1974)]. The results of the fluorography are displayed in FIG. 2. As can be seen, a gp70, p27, and p15 antibodies were found in the serum samples tested.

I claim:

1. A method for recovering virus-free, cell-free Feline leukemia associated neoantigen from cells infected with Feline Leukemia virus, which comprises:
   (a) culturing said cells in a serum-containing growth medium;
   (b) transferring and maintaining said cultured cells in a serum-free medium under conditions and for a time adequate to accumulate said neoantigen shed from said cells in said serum-free medium;
   (c) separating said cultured cells from the associated serum-free medium, thereby producing a cell-free, serum-free medium;
   (d) reducing the volume of said cell-free, serum-free medium without substantial loss of said neoantigen therefrom, thereby producing a neoantigen-rich medium; and
   (e) inhibiting protease enzymes in said neoantigen-rich medium.

2. The method of claim 1 wherein said cultured cells are feline lymphoblastoid cells.

3. The method of claim 1 wherein said cells are separated in step (c) by centrifugation.

4. The method of claim 1 wherein said concentration step (d) includes at least one of the following methods: lyophilization, ultrafiltration, or continuous flow molecular filtration.

5. The method of claim 1 or 3 wherein said concentration step (d) includes continuous-flow molecular filtration with a filter having an exclusion size of about 10,000 daltons to produce a neoantigen-containing retenate followed by freezing and lyophilization of said retenate.

6. The method of claim 1 wherein said inhibition of protease enzymes is effected by adding an effective proportion of a protease enzyme inhibitor.

7. The method of claim 6 wherein said protease enzyme inhibitor comprises at least one of aprotinin, antipapain, leupeptin, ovomucoid, soybean trypsin inhibitor and tolyl-L-lysine chloromethyl ketone.

8. The method of claim 1 wherein said inhibition of protease enzymes is effected by heating said neoantigen to a temperature effective to inhibit protease enzymes therein.

9. The method of claim 1 wherein said inhibition of protease enzymes is effected by changing the pH of said neoantigen to a value effective to inhibit protease enzymes therein.

10. The method of claim 1 wherein said inhibition of protease enzymes is effected by changing the ionic strength of said neoantigens to a value effective to inhibit protease enzymes therein.

11. The neoantigen concentrate produced by the method of claim 1.

12. The neoantigen concentrate produced by the method of claim 5.

13. The neoantigen concentrate produced by the method of claim 6.

* * * * *

REEXAMINATION CERTIFICATE (803rd)
United States Patent [19]
Olsen

[11] B1 4,434,157
[45] Certificate Issued Dec. 29, 1987

[54] METHOD OF RECOVERING CELL ANTIGEN AND PREPARATION OF FELINE LEUKEMIA VACCINE THEREFROM

[75] Inventor: Richard G. Olsen, London, Ohio

[73] Assignee: The Ohio State University Research Foundation, Columbus, Ohio

Reexamination Request:
No. 90/001,225, Apr. 20, 1987

Reexamination Certificate for:
Patent No.: 4,434,157
Issued: Feb. 28, 1984
Appl. No.: 366,352
Filed: Apr. 7, 1982

Related U.S. Application Data

[63] Continuation-in-part of Ser. No. 104,789, Dec. 18, 1979, Pat. No. 4,332,793.

[51] Int. Cl.[4] .............................................. A61K 39/12
[52] U.S. Cl. ...................................................... 424/89
[58] Field of Search ........................................... 424/89

[56] References Cited

U.S. PATENT DOCUMENTS

4,086,134  4/1978  Jarrett et al.

FOREIGN PATENT DOCUMENTS

2951509  7/1980  Fed. Rep. of Germany.

OTHER PUBLICATIONS

Gulyy, M. R., et al., Molekularnaya Biologiya (10), pp. 104–105, (1974) (translation).
Olsen, R. G., et al., Feline Practice 9(4), 16–18 (1979).
Olsen, R. G., et al., In Vitro 12, 37–43 (1976).
Mathes, L. E., et al., Cancer Research 39(3), 950–955 (1979).
Hebebrand, L. C., et al., Cancer Research 39, 443–447 (1979).
Wolff, L. H., et al., J. Natl. Cancer Inst. 58(3), 791–793 (1977).
Log, T., et al., Journal of Immunological Methods 26, 291–303 (1979).
Chem. Abstr. 92:278w (1980); CA92:127481n (1980); CA90:70408w (1979); CA90:52871n (1979); CA90:115352s (1979); CA90:16194k (1979); CA89:71022g (1978); CA89:123142t (1978).
Olsen, R. G., et al., Cancer Research 37, 2082–2085 (1977).
CA88:69685m (1978); CA88:58400p (1978); CA88:48921v (1978); CA86:133639n (1977); CA85:566-79a (1976); CA82:332c (1975); CA80:2063y (1974); CA79:61449f (1973); CA78:93115q (1973); CA77:401w (1972); CA77:83735g (1972); CA70:18482p (1969).
Pinter, A., et al., Virology 83, 417–422 (1977).
Jarrett, W. F. H., Origins of Human Cancer, pp. 1215–1222 (1977).
Wolff, L. H., et al. Journal of Immunological Methods 26, 151–156 (1979).
Pinter, A., et al., Virology 91, 345–351 (1978).
Wolff, L. H., et al., Cancer Research 37, 4134–4137 (Nov. 1977).
Wolff, L. H., "Immunological and Biochemical Characterization of Feline Oncornavirus-Induced Tumor Antigens, Dissertation, Ohio State University, 1977 (published May, 1978).
Pinter, A., et al., Journal of Virology, Apr. 1979, pp. 157–165.
Diaz, J. W., et al., Rev. Cub. Farm., 12, 235–242 (1978).
Giraldi, T., et al., European Journal of Cancer 13, 1321–1323 (1977).
Tweedie, D. J., et al., Biomedicine 29, 1–3 (1978).
Verloes, R., et al., Societe Belge de Biochemie Liege, 23 Oct. 1976, pp. 1119–1121.
Freeman, J. G., et al., Experientia 36, 247–249 (1980).
Lage, A., et al., Neoplasma 25(2) 257–259 (1978).
Latner, A. L., et al., Experimental Cell Biology 47, 392–400 (1979).
Solarino, G., Tumori, Milan 1967, pp. 103–109.
Latner, A. L., et al., Br. J. Cancer 33, 535–538 (1976).
Lozitskii, V. P., et al., Mikrobiologichni. Zhurnal Kiev 1977, 39(6), 751.
Gamba, G., et al., Thrombosis Research 17, 41–53, (1980).
Troll, W., et al., Gesellschaft fuer Biologische Chemie, Colloquim (1979), pp. 165–170.
Thomson, A. W., et al., Br. J. Cancer 35, 454–460 (1977).
Kalaydjiev, V., et al., Zeitschrift fuer Immunitaetsforschung, Allergie und Klinische Immunologie, Stuttgart, 1968, pp. 98–103.
Latner, A. L., et al., Br. J. Cancer 30, 60–67 (1974).
Latner, A. L., et al., Br. J. Cancer 27, 460–464 (1973).
Thomson, A. W., et al., Br. J. Cancer 38, 106–113 (1978).
Whur, P., et al., Br. J. Cancer 28-417–427 (1973).
Goetz, I. E., et al., Cancer Research 32, 2469–2474 (1972).
Parusov, V. I., et al., Patologicheskaia Fiziologia i Eksperimentalnaya Terapiya, 1978, pp. 16–19.
Kalaydjiev, V., et al., International Symposium Vietri sul Mare 1969 (1970), pp. 207–216.
Olsen, R. G., et al., California Veterinarian, Mar. 1980, pp. 11–13.
Volosivets, A. I., et al., Profilaktika osobo opasnykh infektsii, Saratov, vol. 4, pp. 94–98 (1977) (translation).
Koroleva, L. V., Biulletin Eksperimental'noi Biologii Meditsiny, 1969, pp. 41–43.
Tarr, M. J., et al., Chem.-Biol. Interactions 28, 181–199 (1979).
Arora, P. K., Dissertation Abstracts, Int. B Sci. Eng., vol. 40/03, p. 1114–B, Ph. D. Dissertation, 1978.

*Primary Examiner*—Sam Rosen

[57] ABSTRACT

Disclosed in a vaccine which prevents disease caused by Feline leukemia virus (FeLV) and which comprises a protease enzyme-inhibited, cell-free, ostensibly virus-free, in vitro produced feline leukemia neoantigens including FOCMA which evokes an immune response in cats by the appearance of antibodies thereto and a FeLV virion gp70 neoantigen which evokes an immune response in cats by the appearance of antibodies thereto. A novel method for making the vaccine is disclosed also.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-13 is confirmed.

* * * * *